United States Patent
Roman et al.

(10) Patent No.: US 10,450,075 B2
(45) Date of Patent: Oct. 22, 2019

(54) METHOD OF MAKING A MAGNETOSTRICTIVE OSCILLATOR ICE RATE SENSOR PROBE

(71) Applicant: Rosemount Aerospace Inc., Burnsville, MN (US)

(72) Inventors: Jamison K. Roman, Elko, MN (US); Weston Daniel Clarence Heuer, Maple Grove, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 168 days.

(21) Appl. No.: 15/688,840

(22) Filed: Aug. 28, 2017

(65) Prior Publication Data
US 2019/0061958 A1  Feb. 28, 2019

(51) Int. Cl.
| | | |
|---|---|---|
| *B64D 15/20* | (2006.01) | |
| *G01N 29/24* | (2006.01) | |
| *G01B 21/30* | (2006.01) | |
| *G01B 11/30* | (2006.01) | |
| *G08B 19/02* | (2006.01) | |

(52) U.S. Cl.
CPC ............ *B64D 15/20* (2013.01); *G01B 11/30* (2013.01); *G01B 21/30* (2013.01); *G01N 29/2412* (2013.01); *G01N 2291/0251* (2013.01); *G08B 19/02* (2013.01)

(58) Field of Classification Search
USPC .............. 702/54, 127; 73/579; 244/134 F; 340/962
See application file for complete search history.

(56) References Cited

U.S. PATENT DOCUMENTS

| | | | |
|---|---|---|---|
| 4,611,492 A | 9/1986 | Koosmann | |
| 5,922,958 A * | 7/1999 | Schugt ................... | G01N 29/11 73/170.26 |
| 6,269,320 B1 * | 7/2001 | Otto ....................... | B64D 15/20 244/134 C |
| 6,425,286 B1 * | 7/2002 | Anderson .............. | B64D 15/20 73/170.26 |
| 6,560,551 B1 | 5/2003 | Severson et al. | |
| 6,819,265 B2 | 11/2004 | Jamieson et al. | |
| 6,847,903 B2 | 1/2005 | Severson et al. | |
| 7,104,502 B2 | 9/2006 | Otto et al. | |

(Continued)

OTHER PUBLICATIONS

Hoover, Gregory A., "Aircraft Ice Detectors and Related Technologies for Onground and Inflight Applications", Galaxy Scientific Corporation, Apr. 1993, 54 pages.

(Continued)

*Primary Examiner* — John H Le
(74) *Attorney, Agent, or Firm* — Kinney & Lange, P.A.

(57) ABSTRACT

A method of improving the measurement accuracy of a digital ice rate sensor by providing an enhanced surface finish on a magnetostrictive oscillator detector probe by measuring the surface roughness of the detector probe, comparing the measured value to a critical value, and authorizing the probe for use in the digital ice rate sensor if surface roughness is within the critical value. Surface roughness may be measured optically or with a surface profilometer. Remedial steps taken if surface roughness is not within the critical value include reworking the probe surface finish and investigating the manufacturing process.

5 Claims, 5 Drawing Sheets

(56) References Cited

U.S. PATENT DOCUMENTS

| | | | |
|---|---|---|---|
| 9,242,735 B1* | 1/2016 | Meis | B64D 15/20 |
| 2004/0015303 A1 | 1/2004 | Severson et al. | |
| 2005/0218268 A1 | 10/2005 | Otto et al. | |
| 2005/0230553 A1 | 10/2005 | Otto et al. | |
| 2013/0113926 A1* | 5/2013 | Chen | B64D 15/20 |
| | | | 348/135 |
| 2013/0249375 A1* | 9/2013 | Panagotacos | H05B 33/0803 |
| | | | 313/13 |
| 2014/0037446 A1* | 2/2014 | Garnett | B64D 15/14 |
| | | | 416/1 |
| 2015/0103867 A1 | 4/2015 | Meis et al. | |
| 2017/0030848 A1* | 2/2017 | Borigo | B64D 15/20 |

OTHER PUBLICATIONS

Wikipedia, "Surface Roughness", Wikipedia.org, https://en.wikipedia.org/wiki/Surface_roughness, accessed Jul. 10, 2017, 6 pages.
Extended European Search Report dated Jun. 12, 2019, received for corresponding European Application No. 18191235.3.

* cited by examiner

METHOD OF MAKING A MAGNETOSTRICTIVE OSCILLATOR ICE RATE SENSOR PROBE

BACKGROUND

The present invention relates to the measurement of environmental icing conditions, and more particularly, to a method for improving the measurement accuracy of a magnetostrictive oscillator ice rate sensor probe.

Throughout aviation history, icing conditions have been an issue for aircraft. It is a vital part of flight safety to inform the flight crew of ice or icing conditions. The formation of ice as a result of super-cooled liquid water content (LWC) accreting on aircraft surfaces can take place anywhere including engines, air induction systems, and control surfaces. Determining when ice is starting to form or predicting when it will form is important in aircraft management of deicing equipment including heaters, which can consume huge amounts of power. The accurate and timely measurement of liquid water content (LWC) permits prompt signaling for alerting the flight crew, activating deicing systems, and for data gathering and reporting.

As technology has advanced, improved methods of ice detection have been developed, with a variety of different technologies that have been or currently are deployed. A current method that is employed to measure LWC utilizes a magnetostrictive oscillator (MRO) vibrating probe that extends into the airstream, with a driving circuit that senses the resonant frequency of the probe. For example, Severson, et. al., U.S. Pat. No. 6,560,551 discloses a vibrating probe type ice detector. The ice growth rate is predictably variable over an accretion cycle based upon the incremental rate of change of the vibrating probe's frequency throughout the sensing cycle. The time rate of change of resonant frequency df/dt throughout the ice accretion cycle is determined. As ice accretes on the probe, the probe's resonant frequency decreases due to the increase in mass. At the end of the ice accretion cycle a heater internal to probe is energized to rapidly melt the ice on the surface on the probe. As the ice melts from the probe, the resonant frequency rapidly increases back to the nominal resonant frequency. The heater is deenergized, the probe surface rapidly returns to an equilibrium condition with the ambient conditions, and the next ice accretion cycle begins.

The physical dimensions and mass of the probe may vary widely from one design to another, with these values contributing to the nominal resonant frequency of a particular design. For example, the Rosemount Icing Detector Model 871 is designed to have a nominal resonant frequency of 40.0 KHz. This exemplary design is one of many that are available in the aviation industry. In this exemplary ice detector, an ice accretion cycle begins with the resonant frequency at 40.0 KHz and the frequency decreases as ice accumulates on the ice detector probe. The time rate of change of resonant frequency df/dt is measured during the ice accretion cycle, with the cycle ending when the resonant frequency decreases to 39.7 KHz. At the end of this cycle, the probe heater is energized to melt the accumulated ice. Under some conditions, the accretion cycle will be ended prior to reaching this ending resonant frequency. The period of the accretion cycle will vary widely, and will depend on multiple factors including the ambient temperature, density, pressure, LWC, and airspeed. The accretion cycle period may range from a few seconds through several minutes, or longer.

A problem with MRO ice rate sensor systems is that their system accuracy may often worse than 20%, which may be considered unsatisfactory for certain applications. Knowing with accuracy when icing conditions exist, and therefore accurately measuring the liquid water content of the airstream near the aircraft during flight operation, is important because of the adverse effect that icing has on aircraft performance and safety. Several attempts to improve the measurement accuracy of vibrating probe ice rate sensors have been deployed. For example, Otto, et. al., U.S. Pat. No. 7,104,502 discloses a probe support strut containing one or more features which allow the probe to accrete ice at a higher temperature than would conventionally be possible.

Despite many improvements that have been advanced in this field, there is an ongoing need to improve the overall accuracy of the MRO digital ice rate sensor. A design target for an MRO digital ice rate sensor is to measure the LWC in situ with an accuracy of 20%. Achieving this target will enable an aircraft flight crew to operate within a flight envelope that minimizes the adverse effects of icing, some of which have been described above.

SUMMARY

According to one embodiment of the present disclosure, a method of improving the measurement accuracy of a digital ice rate sensor is disclosed, the method being measuring the surface roughness of the magnetostrictive oscillator detector probe, comparing the value measured to a critical value, and taking one or more remedial actions if the value measured is greater than the critical value, before using the finished magnetostrictive oscillator detector probe in a digital ice rate sensor.

DETAILED DESCRIPTION

Figure 1A:
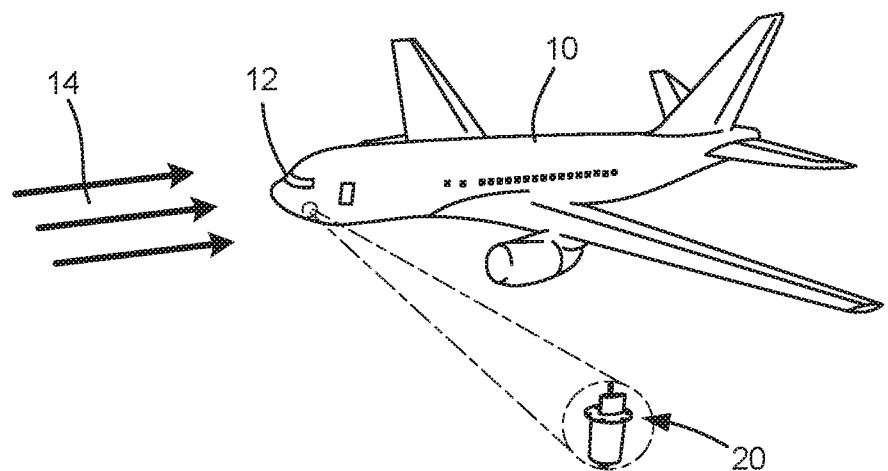
FIG. 1A is a perspective view depicting a location of a magnetostrictive oscillator ice rate sensor on an aircraft.

FIG. 1A is a perspective view depicting a location of a magnetostrictive oscillator (MRO) ice rate sensor 20. Depicted in FIG. 1A is aircraft 10, cockpit 12, airstream 14, and MRO ice rate sensor 20. In the embodiment shown, the mounting location for MRO ice rate sensor 20 is on the forward region of aircraft 10, in the vicinity of cockpit 12. MRO ice rate sensor 20 senses the liquid water content (LWC) contained in airstream 14 which aircraft 10 is entering, to provide the most realistic in situ measurement of LWC contained in airstream 14. A location for MRO ice rate sensor 20 near the forward region of aircraft 10 minimizes the disruption and possible heating effect of aircraft 10 on airstream 14, which may occur by the passage of aircraft 10 through the atmosphere. Moreover, because avionics control systems and indicators are typically located near cockpit 12, with electrical cables (not shown) being used to interconnect the various components of the digital ice rate sensor system (not shown), locating MRO ice rate sensor 20 near cockpit 12 reduces the lengths of cables used in connecting the associated components. In the illustrated embodiment, a single MRO ice rate sensor 20 is located on a fixed-wing commercial passenger aircraft 10. In another embodiment, two MRO ice rate sensors 20 may be installed on aircraft 10 near cockpit 12 for redundancy or for other reasons. In other further embodiments, more than two MRO ice rate sensors 20 may be installed on aircraft 10, with some of the installation locations possibly being at other locations on aircraft 10. In further embodiments, aircraft 10 may be a logistics aircraft, military aircraft, rotary wing aircraft, blimp, dirigible, weather balloon, or other atmospheric or space-based research equipment, or any other platform. Moreover, MRO ice rate sensor 20 may be installed on any ground-based system including wind tunnels, scientific facilities, and manufacturing operations, where it is desirable to measure liquid water content in any airstream 14, whether natural or artificially created.

Figure 1B:
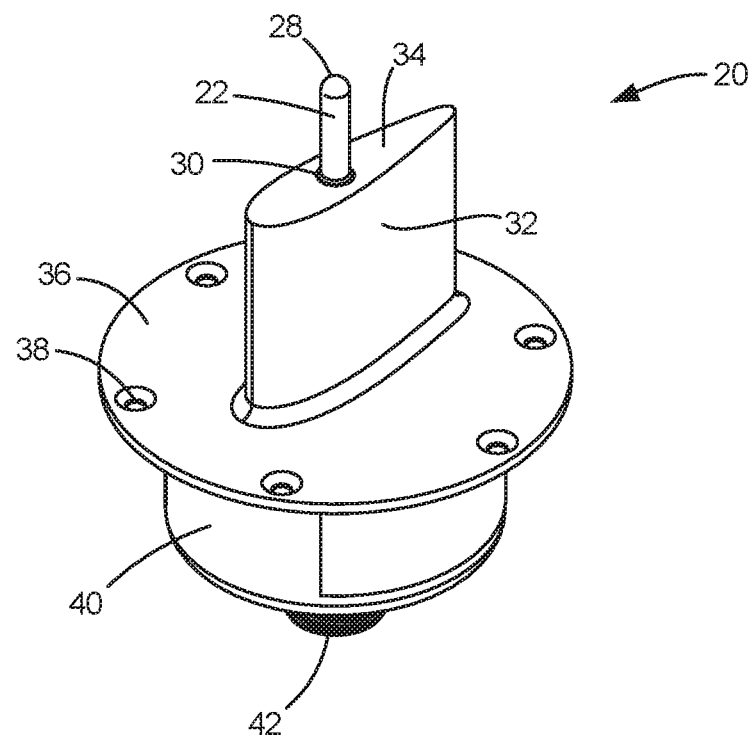
FIG. 1B is a perspective view of the magnetostrictive oscillator (MRO) ice rate sensor.

FIG. 1B is a perspective view depicting MRO ice rate sensor 20. Shown in FIG. 1B is probe 22, probe tip 28, collar 30, support strut 32, strut distal end 34, flange 36, a plurality of mounting apertures 38, recessed body 40, and electrical connection 42. MRO ice rate sensor 20 may be mounted on aircraft 10 (shown in FIG. 1A). In an embodiment, probe 22 may be comprised of a metallic alloy and the outer surface of probe 22 may plated with a metal. In an embodiment, nickel may be used to plate the outer surface of probe 22. In an embodiment, threaded fasteners (not shown) may be used to attach flange 36 to the skin of aircraft 10 via mounting apertures 38. Those skilled in the art of avionics are familiar with various means of attaching sensors to aircraft 10, with threaded fasteners being generally accepted to facilitate removal for maintenance and other purposes.

In the illustrated embodiment, support strut 32 extends outward from flange 36, supporting probe 22 at strut distal end 34 by means of collar 30 located on strut distal end 34. Support strut 32 positions probe 22 in airstream 14. Support strut 32 provides a stand-off distance between probe 22 and the region proximal the skin of aircraft 10 to minimize the effects of the boundary layer flow of air along the skin of aircraft 10. Probe tip 28 is at the outward end of probe 22, distal from support strut 32. In the illustrated embodiment, probe trip 28 is rounded, forming an approximately hemispherical shape. In other embodiments probe tip 28 may have other geometries.

Collar 30 is located on strut distal end 34, providing support for probe 22 while also isolating probe 22 from support strut 32. In an embodiment, collar 30 may provide thermal and vibrational isolation for probe 22 from support strut 32. In the illustrated embodiment, the axis of probe 22 extends from support strut 32 approximately perpendicular to the surface of strut distal end 34. In other embodiments, the axis of probe 22 may form another angle to the surface of strut distal end 34. Recessed body 40 encloses various electrical circuits (not shown) that are used by MRO ice rate sensor 20, and electrical connection 42 allows for an electrical cable (not shown) to connect MRO ice rate sensor 20 to a digital computer (shown in FIG. 2). During operation of the digital ice rate sensor system (not shown), electronic circuitry located within recessed body 40 drive probe 22 to oscillate at resonant frequency f. An electrical heater (not shown) is contained within probe 22. Electronic circuitry (not shown) contained within recessed body 40 periodically energize the electrical heater contained within probe 22 during the de-ice operation that occurs at the end of each ice accretion cycle (described later, in FIG. 2). Electronic circuitry contained within recessed body 40 detects the time rate of change of resonant frequency df/dt as ice accretes on probe 22 (described later, in FIG. 2).

Figure 2:
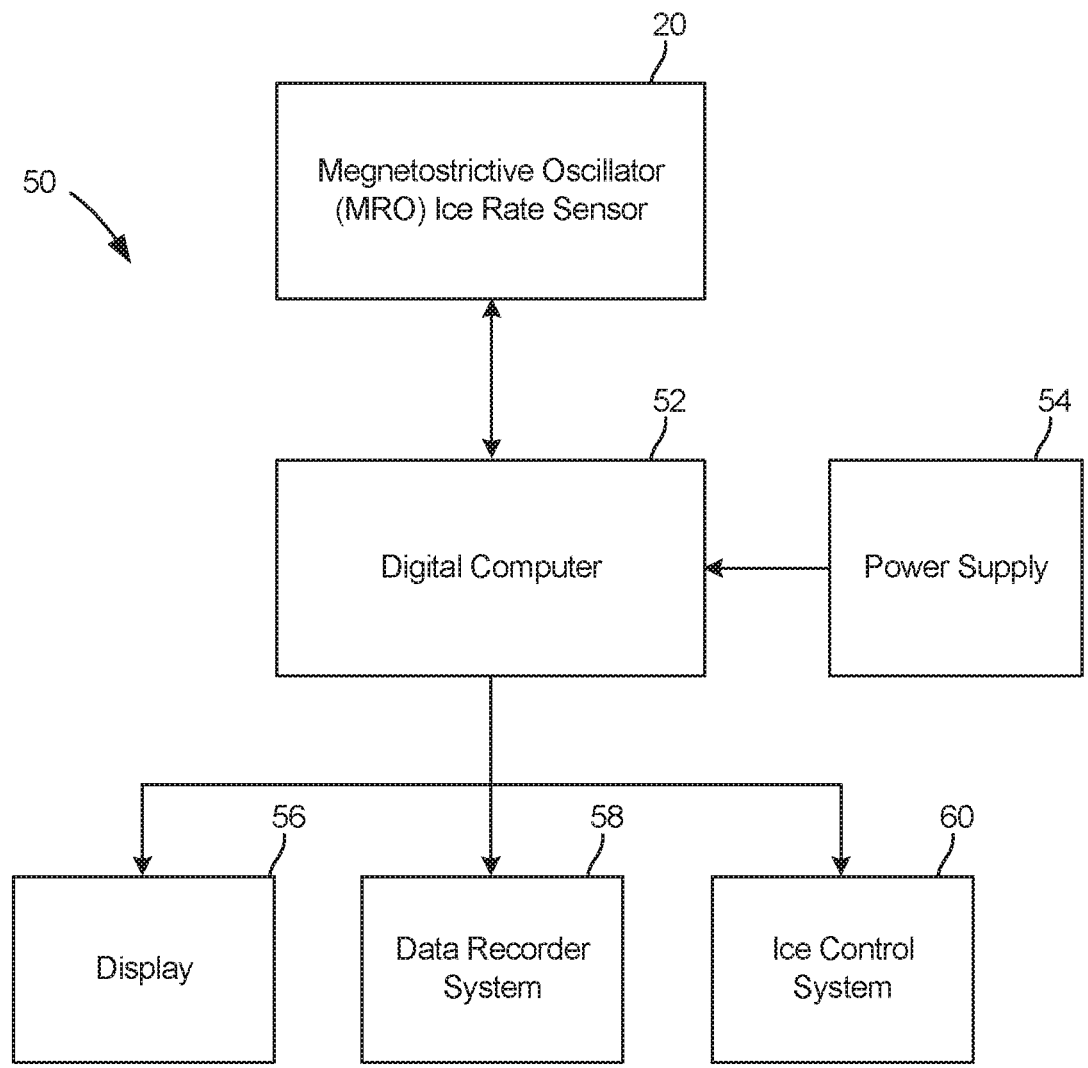
FIG. 2 is a schematic block diagram of components of a digital ice rate sensor system.

FIG. 2 is a schematic block diagram depicting the major components of digital ice rate sensor system 50. The embodiment shown in FIG. 2 includes digital computer 52, power supply 54, MRO ice rate sensor 20, display 56, data recorder system 58, and ice control system 60. Power supply 54 receives power from the onboard electrical system of aircraft 10 and provides electrical power to digital computer 52, which may be installed anywhere on board aircraft 10 (shown in FIG. 1A). Digital computer 52 is connected by cable (not shown) to MRO ice rate sensor 20, thereby providing power and control to MRO ice rate sensor 20 while also receiving signals from MRO ice rate sensor 20. Digital computer 52 is connected to display 56, data recorder system 58, and ice control system 60. During operation of digital ice rate sensor system 50, MRO ice rate sensor 20 performs an ice accretion cycle while measuring the resonant frequency f of probe 22. Ice (not shown) accretes on probe 22 as a result of the super-cooled LWC contained within airstream 14. As ice accretes on probe 22, resonant frequency f of probe 22 decreases as a result of the increase in effective mass of probe 22 caused by the accretion of ice on probe 22. Digital computer 52 calculates the time rate of change of resonant frequency df/dt of probe 22 during the ice accretion cycle. Digital computer 52 may calculate a plurality of parameters based on the time rate of change of resonant frequency df/dt, including, for example, values representing icing rate and the liquid water content (LWC) in airstream 14 (shown in FIG. 1A). Digital computer 52 provides input to display 56, providing a visual display of various parameters for the crew of aircraft 10. In an embodiment, display 56 may be a digital readout. In another embodiment, display 56 may be a warning light indicating to the aircrew that a specified icing condition exists. In an embodiment, more than one display 56 may be provided, and displays 56 may be located at various locations on aircraft 10. Digital computer 52 provides input to data recorder system 58. In an embodiment, data recorder system 58 may be the flight data recorder. Digital computer 58 provides input to ice control system 60. In an embodiment, ice control system 60 may be components on the skin of aircraft 10 including wings, flaps, ailerons, rudders, and other critical surfaces. In an embodiment, ice control system 60 may energize resistive heaters (not shown) used to melt ice buildup on outer surfaces of aircraft 10. In another embodiment, ice control system 60 may be an inflatable boot (not shown) used to break up ice on outer surfaces of aircraft 10. Those skilled in the art of aviation ice control systems are familiar with various means that may be used for controlling or reducing the buildup of ice on various airborne vehicles.

Figure 3:
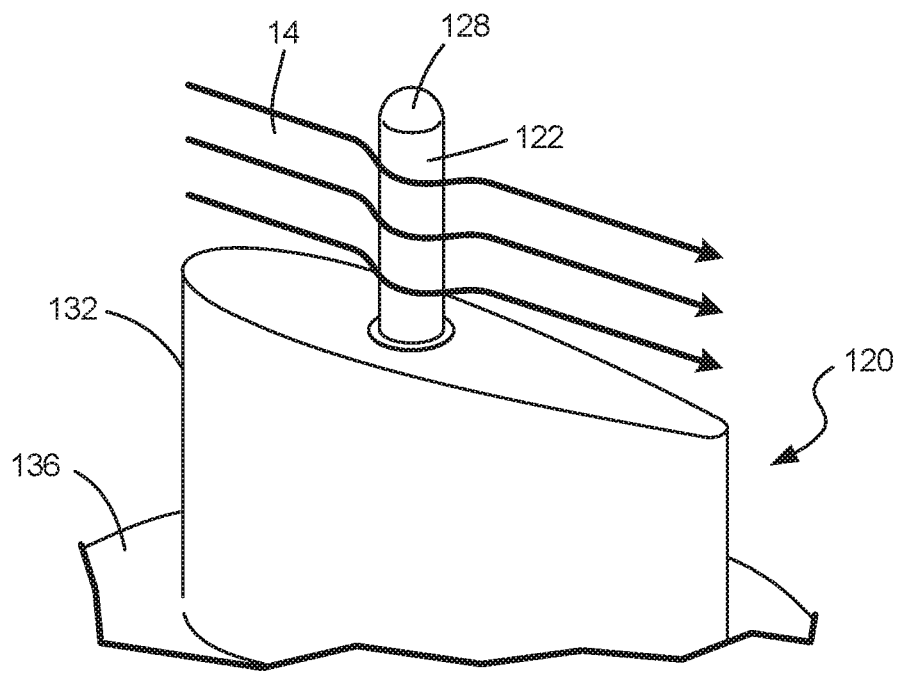
FIG. 3 is a perspective schematic of an airstream flowing over the magnetostrictive oscillator ice rate sensor probe and strut assembly.

FIG. 3 is a perspective schematic of airstream 14 over probe 122 of the MRO ice rate sensor 120 of the prior art. Shown in FIG. 3 is probe 122, probe tip 128, collar 130, support strut 132, strut distal end 134, flange 136, and airstream 14. Similar to the description in FIG. 1B, a metal such as nickel may coat the outer surface of probe 122. Similar to the description in FIG. 1B, support strut 132 extends probe 122 away from the skin of aircraft 10 (shown in FIG. 1A), being attached to aircraft by flange 136. Probe 122 is supported at strut distal end 134 by collar 130. Airstream 14 flows over probe 122 as aircraft 10 travels through the atmosphere. Super-cooled liquid water content (LWC) in airstream 14 accretes ice (not shown) on probe 122, thereby increasing the effective mass of probe 122. Probe 122 vibrates at resonant frequency f, as described in FIG. 1B.

As ice accretes on probe 122 from the super-cooled LWC contained in airstream 14, the effective mass of probe 122 increases, thereby lowering resonant frequency f. Digital computer calculates ice accretion rate by measuring the time rate of change of resonant frequency df/dt. Digital computer 52 may also calculate the LWC of airstream 14, and other related parameters. After resonant frequency f reduces to a specified frequency, digital computer 52 terminates the ice accretion cycle by performing a de-icing cycle. During the de-icing cycle, an electrical heater (not shown) within the interior of probe 122 is energized from circuitry contained within recessed body (not shown), thereby causing probe 122 to melt ice that has thereon accreted. The ice accretion and de-icing cycles are thereafter repeated. In an embodiment, digital computer 52 may continuously perform the ice accretion and de-icing cycles during flight operations, providing for continuous operation of digital ice rate sensor system during operation of aircraft 10.

Figure 4:
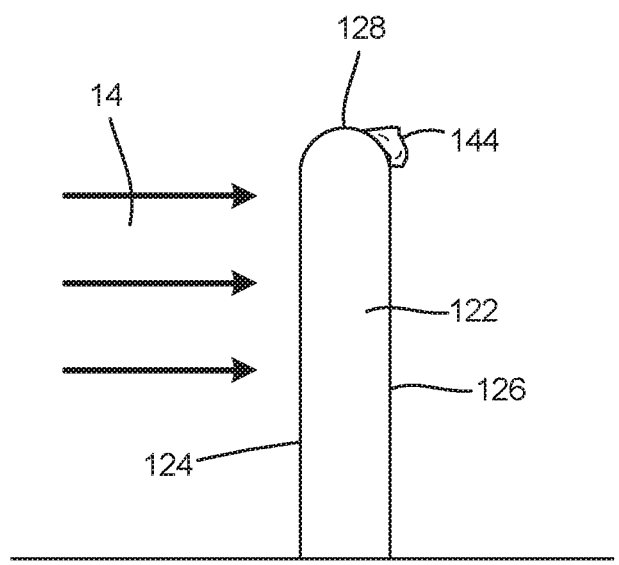
FIG. 4 is a side view schematic of the magnetostrictive oscillator ice rate sensor probe in an airstream containing liquid water content.

FIG. 4 is a side view diagram of probe 122 of the prior art in an airstream 14 containing super-cooled LWC. Depicted in FIG. 4 is probe 122, probe tip 128, probe leading edge 124, probe trailing edge 126, airstream 14, trapped water 144, and strut distal end 134. The arrangement of probe 122 is similar to that described under FIG. 3. During flight of aircraft 10 (shown in FIG. 1A), probe 122 is located in airstream 14 which flows over probe 122 from probe leading edge 124 to probe trailing edge 126. Airstream 14 contains super-cooled LWC, causing ice (not shown) to accrete on probe 122. The de-ice cycle described under FIG. 3 raises the temperature of probe 122, thereby causing accreted ice to melt. Under some conditions, airstream 14 may remove all melted ice from probe 122. As airstream 14 flows over probe 122 and probe tip 128, a negative pressure region is created near probe trailing edge 126 in the area proximate probe tip 128. Under some conditions, airstream 14 does not fully remove all melted ice from probe 122 in the region proximate probe tip 128, thereby allowing liquid water 144 to remain trapped on probe trailing edge 126 in the area proximate probe tip 128. Liquid water 144 trapped after the de-ice cycle causes an erroneous measurement of the ice rate by MRO ice rate sensor 120, thereby contributing to the overall system inaccuracy of the digital ice rate sensor system of the prior art (not shown). The overall accuracy of digital ice rate sensor system is desired to be 20% or less, which may be considered acceptable for certain applications. An overall accuracy of digital ice rate sensor system worse than 20% may be considered unacceptable under some conditions. In the prior art, various factors contributing to the phenomenon of liquid water 144 remaining trapped on probe tip 122 following the de-ice cycle include unspecified values of surface roughness $R_a'$ (shown in FIG. 5) of probe 122. Accordingly, unspecified values of surface roughness $R_a'$ of probe 122 may contribute to an overall digital ice rate sensor system accuracy being worse than 20%.

During testing, observations were performed on rounded tip 128 of probe 122 of the prior art. It was demonstrated that conditions in ground-based wind tunnels could simulate conditions whereby a mass of liquid water 144 remains on probe 122, particularly on probe trailing edge 126 proximate probe tip 128, following the initial de-icing cycle. The runback liquid water 144 would remain attached to probe 122 at low airspeeds, and would require additional time to re-freeze after the probe heater was de-energized. Frequency response plots showed a unique trough in the frequency vs. time plot with this trough phenomenon correlating to the attached liquid water 144 during the period of time that the water was in a liquid state. When liquid water 144 would re-freeze, the trough phenomena on the frequency would diminish. The existence and characteristics of this frequency response phenomenon, including, for example, the behavior of time rate of change of resonant frequency df/dt, were correlated to error of MRO ice rate sensor 120, generally causing the measurement error to exceed the 20% desired value.

Figure 5:
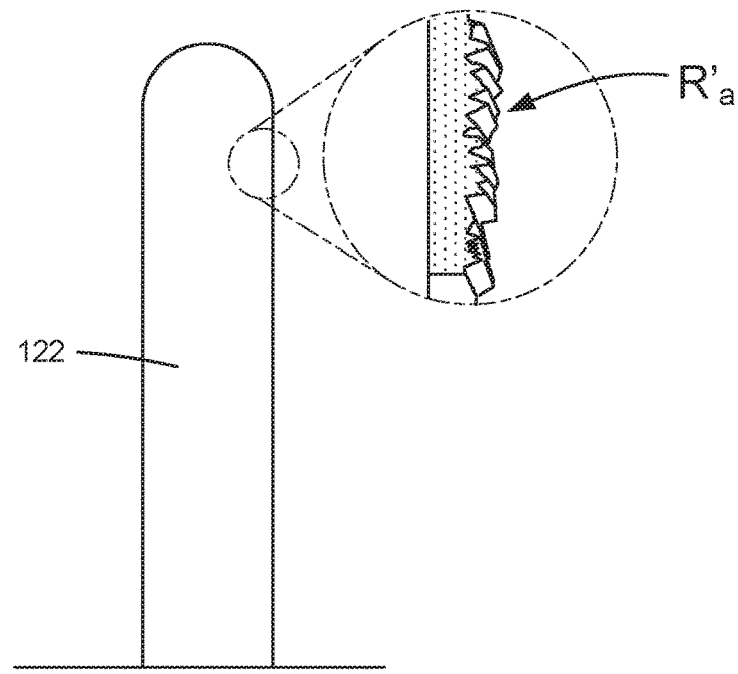
FIG. 5 is a side view of the magnetostrictive oscillator ice rate sensor probe with an enlargement illustrating the unspecified surface finish.

FIG. 5 is a side view of probe 122 of MRO ice rate sensor 120 of the prior art, with an enlargement section illustrating the unspecified surface roughness $R_a'$ of probe 122. Values of unspecified surface roughness $R_a'$ vary considerably, and may be affected my variations that exist in the manufacturing process where probe 122 is produced. Examples of the factors contributing to excessive values of $R_a'$ include variations in the production of the alloy stock used for probe 122, variations in the process of machining the outer surface of probe 122, and variations in the coating or plating process used to apply a metal (not shown) on the exterior surface of probe 122. In the prior art, as depicted in FIG. 5, the value of surface roughness $R_a'$ may be a significant value, however it may not be specified.

Figure 6:
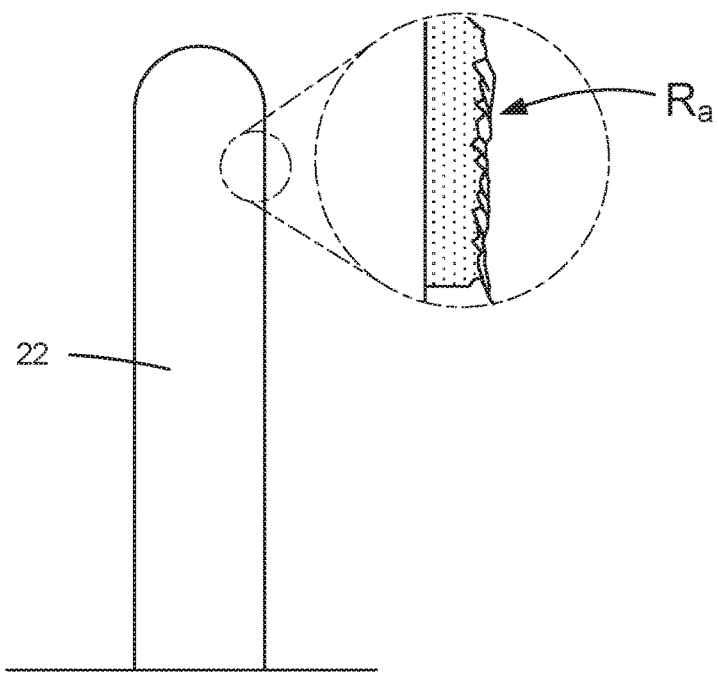
FIG. 6 is a side view of the magnetostrictive oscillator ice rate sensor probe with an enlargement illustrating an enhanced surface finish of the present disclosure.

FIG. 6 is a side view of probe 22 of MRO ice rate sensor 20 (shown in FIG. 1B) of the present disclosure, with an enlargement illustrating the surface roughness $R_a$ as produced under the method of the present disclosure. Also shown in FIG. 6 is probe tip 28. Depicted in FIG. 6 is surface roughness $R_a$ having a value at or lower than the critical value of surface roughness $R_c$ such that a negligible amount of liquid water (not shown) remains in probe 22 following the de-ice cycle. In an embodiment, an optical instrument may be used to measure surface roughness $R_a$. In another embodiment, a surface profilometer may be used to measure surface roughness $R_a$. In one embodiment, the measured value of surface roughness $R_a$ may be taken at a particular location on probe 22, for example, near probe tip 28. In another embodiment, multiple measurements of surface roughness $R_a$ may be taken over various locations on the surface of probe 22. In an embodiment, the multiple measurements of surface roughness $R_a$ maybe mathematically averaged to produce an overall measured value of surface roughness $R_a$. In another embodiment, the maximum value of any single measurement of surface roughness $R_a$ may be used to determine the working value of measured surface roughness $R_a$. In an embodiment, surface roughness $R_a$ refers to the arithmetical mean deviation of the assessed surface profile of probe 22. In other embodiments, for example, $R_q$ (root mean square), $R_v$ (maximum valley depth), $R_p$ (maximum peak height), $R_t$ (maximum height of the profile), $R_{sk}$ (roughness skewness), and $R_{ku}$ (roughness kurtosis) may be used to represent the value of surface roughness. Those who are skilled in the art of measuring surface roughness are familiar with these various measures of surface roughness.

In an embodiment, a critical value of surface roughness $R_c$ is established based on the particular measurement convention being used for surface roughness $R_a$. Critical value of surface roughness $R_c$ is established by determining the value of surface roughness $R_a$ that produces negligible liquid water (not shown) being trapped near the probe tip 28 following the de-ice cycle. In an embodiment, critical value of surface roughness $R_c$ may be determined by wind tunnel evaluation of the particular probe 22 being used. In another embodiment, critical value of surface roughness $R_c$ may be determined by evaluating the behavior of the rate of frequency during an ice accretion cycle.

Extensive experimentation has determined that uncontrolled probe surface roughness contributes to the overall system inaccuracy of the digital ice rate sensor system. The present disclosure improves the accuracy of MRO ice rate sensor 20 by providing a manufacturing process for controlling surface roughness $R_a$ of probe 22 to within critical value of surface roughness $R_c$. Based on testing, the present disclosure is estimated to improve the accuracy of the MRO ice rate sensor 20 (shown in FIG. 1A) to 20% or less, which may meet the design target for modern aviation applications.

Extensive testing was performed on MRO ice rate sensors, with root cause analysis being performed on the source of errors in the LWC measurement. Controlled conditions were established in ground-based systems that duplicate a broad range of aeronautical flight conditions. Ground-based systems that were used included both a Production Icing Wind Tunnel and the Rosemont Transonic Wind Tunnel, in which various LWC conditions can be created with high precision. In an embodiment of the present disclosure, the value of surface roughness Ra is equal to or less than the critical value of surface roughness Rc for the contribution of probe 22 to the overall accuracy of MRO ice rate sensor 20 to be negligible. Notably, as depicted in FIG. 6, the value of surface roughness $R_a$ is less than the value of surface roughness $R_a'$ as in the prior art.

Figure 7:
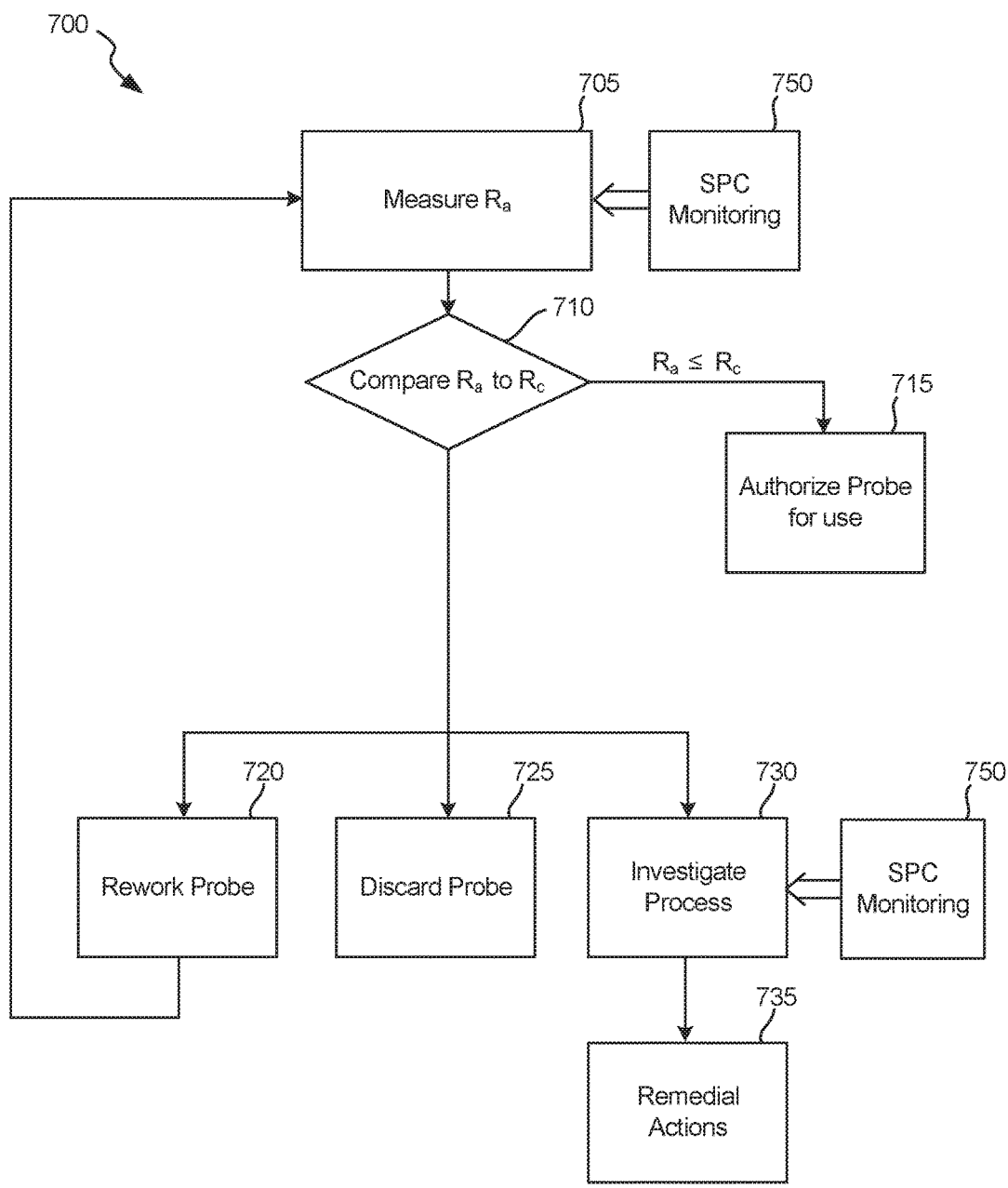
FIG. 7 is a flow chart of the process steps implementing the method of providing the enhanced surface finish.

FIG. 7 is a flow chart of the process steps 700 for implementing the method of the present disclosure. At step 705, surface roughness $R_a$ is measured. At step 710, surface roughness $R_a$ is compared to the critical value of surface roughness $R_c$. At step 715, the probe is authorized for use. At step 720, the probe is re-worked. At step 725, the probe is discarded. At step 730, the probe manufacturing process is investigated. At step 735, remedial actions are taken. At steps 750, statistical process control (SPC) monitoring is performed. During the process of manufacturing probe 22 for use in MRO ice rate sensor 20, the outer surface of probe 22 is inspected following the metal plating process (not shown) and prior to final assembly into MRO ice rate sensor 20. At step 705, surface roughness $R_a$ is measured on probe 20. In an embodiment, an optical instrument may be used to measure surface roughness $R_a$. In another embodiment, a surface profilometer may be used to measure surface roughness $R_a$. In one embodiment, the measured value of surface roughness Ra may be taken at a particular location on probe 20, for example, near probe tip 28. In another embodiment, multiple measurements of surface roughness $R_a$ may be taken across the surface of probe 20. In an embodiment, the multiple measurements of surface roughness $R_a$ may be mathematically averaged to produce an overall measured surface roughness $R_a$. In another embodiment, the maximum value of any single measurement of surface roughness $R_a$ may be used to determine the ultimate value of measured surface roughness $R_a$. As used here, surface roughness $R_a$ refers to the arithmetical mean deviation of the assessed surface profile. In other embodiments, other measures of surface roughness may be used. For example, $R_q$ (root mean square), $R_v$ (maximum valley depth), $R_p$ (maximum peak height), $R_t$ (maximum height of the profile), $R_{sk}$ (roughness skewness), and $R_{ku}$ (roughness kurtosis) may be used.

The critical value for surface roughness $R_c$ will be known based on the particular measurement methodology of a particular embodiment and a determination of the critical value for surface roughness $R_c$ that minimizes liquid water remaining on probe 22 following a de-icing cycle (not shown). The critical value for surface roughness $R_c$ will depend on various factors including the physical dimensions of probe 22 and the metal used to coat the exterior surface of probe 22 in a particular embodiment. Moreover, the method of measuring surface roughness $R_a$ may affect the critical value for surface roughness $R_c$. The decision box at step 710 compares the measured value of surface roughness $R_a$ to the critical value of surface roughness $R_c$ that has been established. If $R_a$ is less than or equal to $R_c$, the particular probe 22 being evaluated is allowed to step 715 wherein the probe is authorized for use. However, if $R_a$ exceeds $R_c$, step 720 is entered wherein the probe is reworked. In an embodiment, step 720 is performed in an attempt to bring $R_a$ into specification. In another embodiment, probe 22 may be discarded at step 725. In an embodiment, reworking probe 22 at step 720 may consist of polishing probe 22. Polishing may be a mechanical operation, or it may be a chemical mechanical operation. In an embodiment, the final metallic coating on probe 22 may be removed and then reapplied as part of step 720.

In an embodiment, if $R_a$ exceeds $R_c$ at step 710, an investigation may be performed on the manufacturing process for probe 22 at step 730. Specific areas that are investigated under step 730 may include the metallic plating process of probe 22, including measuring the temperature, soak time, and chemical concentration of the plating bath (not shown). As an outcome of step 730, remedial actions may be taken at step 735. In step 735, remedial actions may include modifying the temperature, soak time, and chemical concentration of the plating bath (not shown). In an embodiment, step 735 remedial actions may include replacing the plating bath solution with a new solution. After remedial actions are taken in step 735, step 720 may continue whereby probe 22 may be reworked. The flowchart then directs probe 22 back to step 705 for measuring $R_a$.

In an embodiment, step 750 may implement statistical process control (SPC) monitoring. In the process flow depicted in FIG. 7, SPC monitoring under step 750 may be performed continuously on various parameters existing in the manufacturing process for probe 22. In an embodiment, a sampling methodology representative of the general manufacturing environment may be used performing SPC monitoring under step 750. Parameters monitored in step 750 may include temperature, soak time, and concentration of the plating bath solution. A trend plot of the measured parameters may be used to indicate the impending need for remedial actions to be taken at step 735, even in the absence of $R_a$ exceeding $R_c$ in step 710. In an embodiment, step 750 may also include monitoring measured values of $R_a$ on each probe 22 produced, with SPC trend analysis being used in SPC monitoring at step 750 even though $R_a$ does not exceed $R_c$ at step 710. In an embodiment, step 750 may include the measuring parameters, recording parameters, evaluating the series of recorded parameters, and evaluating the series of recorded parameters. In a further embodiment, step 750 may include evaluating the series of recorded parameters to identify trends in the series of recorded parameters, calculating control limits, and calculating alarm limits for the various recorded parameters.

Description of Possible Embodiments

The following are non-exclusive descriptions of possible embodiments of the present invention.

A method of improving the measurement accuracy of a digital ice rate sensor by providing an enhanced surface finish on a magnetostrictive oscillator detector probe according to an exemplary embodiment of this disclosure, among other possible things, includes measuring external surface roughness on the magnetostrictive oscillator detector probe; comparing a value of the measured external surface roughness to a critical value; taking at least one remedial action if the value of the measured external surface roughness is greater than the critical value; repeating the step of measuring the external surface roughness on the magnetostrictive oscillator detector probe at least one time after the at least one remedial action is taken; and authorizing the magnetostrictive oscillator detector probe for use on the digital ice rate sensor if the value of the measured external surface roughness is not greater than the critical value.

The method of the preceding paragraph can optionally include, additionally and/or alternatively, any one or more of the following features, configurations and/or additional components:

A further embodiment of the foregoing method, wherein the measuring is performed using an optical instrument.

A further embodiment of the foregoing method, wherein the measuring is performed using a surface profilometer.

A further embodiment of the foregoing method, wherein the value of the measured external surface roughness is an average value of more than one measurement.

A further embodiment of the foregoing method, wherein the at least one remedial action comprises reworking the magnetostrictive oscillator detector probe.

A further embodiment of the foregoing method, wherein the at least one remedial action comprises investigating the magnetostrictive oscillator detector probe manufacturing process.

A method of improving the measurement accuracy of digital ice rate sensors by providing an enhanced surface finish on magnetostrictive oscillator detector probes, further comprising a method a of statistical process control, comprising the steps of: measuring external surface roughness on each of the magnetostrictive oscillator detector probes and at least one parameter of a metal plating bath, wherein the at least one parameter is selected from the group consisting of bath temperature, soak time, and chemical concentration, and wherein the measuring occurs on at least a sample of the magnetostrictive oscillator detector probes; recording the external surface roughness and the at least one parameter; evaluating a series of the external surface roughness and the at least one parameter; and determining a trend in the series.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of improving the measurement accuracy of a digital ice rate sensor by providing an enhanced surface finish on a magnetostrictive oscillator detector probe, comprising the steps of:
   measuring external surface roughness on the magnetostrictive oscillator detector probe;
      wherein the measuring is performed using equipment that is selected from the group consisting of an optical instrument and a surface profilometer;
   comparing a value of the measured external surface roughness to a critical value;
   taking at least one remedial action if the value of the measured external surface roughness is greater than the critical value;
      wherein the at least one remedial action is selected from the group consisting of:
         mechanically polishing the magnetostrictive oscillator detector probe; and
         removing and reapplying a metallic coating on the magnetostrictive oscillator detector probe;
   repeating the step of measuring the external surface roughness on the magnetostrictive oscillator detector probe at least one time after the at least one remedial action is taken; and
   authorizing the magnetostrictive oscillator detector probe for use on the digital ice rate sensor if the value of the measure external surface roughness is not greater than the critical value.

2. The method of claim 1, wherein the value of the measured external surface roughness is an average value of more than one measurement.

3. The method of claim 1, wherein the at least one remedial action comprises investigating the magnetostrictive oscillator detector probe manufacturing process.

4. A method of improving the measurement accuracy of digital ice rate sensors by providing an enhanced surface finish on a magnetostrictive oscillator detector probes, further comprising a method of statistical process control, comprising the steps of:
   measuring external surface roughness on each of the magnetostrictive oscillator detector probes and at least one parameter of a metal plating bath, wherein:
      the measuring is performed using equipment that is selected from the group consisting of an optical instrument and a surface profilometer; and
      the at least one parameter is selected from the group consisting of bath temperature, soak time, and chemical concentration, and wherein the measuring occurs on at least a sample of the magnetostrictive oscillator detector probes;
   recording the external surface roughness and the at least one parameter;
   evaluating a series of the external surface roughness and the at least one parameter; and
   determining a trend in the series.

5. The method of claim 4, wherein a value of the measured external surface roughness is an average value of more than one measurement.

* * * * *